(12) United States Patent
Schulz

(10) Patent No.: US 12,108,935 B2
(45) Date of Patent: Oct. 8, 2024

(54) ALBARRAN MODULE AND METHOD FOR BRACING A PULL WIRE

(71) Applicant: OLYMPUS WINTER & IBE GMBH, Hamburg (DE)

(72) Inventor: Kevin Alexander Schulz, Wilstedt (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 212 days.

(21) Appl. No.: 17/170,179

(22) Filed: Feb. 8, 2021

(65) Prior Publication Data

US 2021/0244264 A1 Aug. 12, 2021

(30) Foreign Application Priority Data

Feb. 6, 2020 (DE) ...................... 10 2020 103 016.9

(51) Int. Cl.
 *A61B 1/00* (2006.01)
 *A61B 1/005* (2006.01)
 *A61B 1/018* (2006.01)

(52) U.S. Cl.
 CPC ...... *A61B 1/00098* (2013.01); *A61B 1/00066* (2013.01); *A61B 1/0008* (2013.01); *A61B 1/0057* (2013.01); *A61B 1/018* (2013.01)

(58) Field of Classification Search
 CPC .............. A61B 1/00066; A61B 1/0008; A61B 1/00098; A61B 1/005; A61B 1/0051; A61B 1/0052; A61B 1/0053; A61B 1/0055; A61B 1/0056; A61B 1/0057; A61B 1/0058; A61B 2017/00318; A61B 2017/00323; A61B 2017/00327; A61M 25/0136; A61M 25/0147
 See application file for complete search history.

(56) References Cited

U.S. PATENT DOCUMENTS 6,699,183 B1 * 3/2004 Wimmer .............. A61B 1/0057
 600/149
2018/0168435 A1 6/2018 Akhoondi et al.

FOREIGN PATENT DOCUMENTS

DE 29605328 U1 6/1996
DE 19627016 C1 2/1998
DE 10 2012 009 332 A1 11/2013
FR 2524595 A1 10/1983

* cited by examiner

*Primary Examiner* — Ryan N Henderson
(74) *Attorney, Agent, or Firm* — Oliff PLC

(57) ABSTRACT

An Albarran module, a drive body, and a method for bracing a pull wire, by which method at least one pull wire can be braced in a simple and reliable manner by a tensioning means for bracing the at least one pull wire is connectable to a drive body of the Albarran module parallel to a longitudinal axis of a shaft. The Albarran module has an Albarran lever at a distal end of a shaft. The Albarran lever is actuatable via a toggle on a main body of the Albarran module. For this purpose, the lever is coupled mechanically to the toggle by pull wires along the shaft. In known Albarran modules, the fitting and bracing of these pull wires proves complicated and laborious.

7 Claims, 2 Drawing Sheets

ALBARRAN MODULE AND METHOD FOR BRACING A PULL WIRE

The invention relates to an Albarran module according to the preamble of claim 1. The invention further relates to a drive body according to claim 8. The invention additionally relates to a method for bracing a pull wire, for actuation of an Albarran lever of an Albarran module, according to the preamble of claim 9.

Albarran modules are used as aids when performing operations or treatment procedures with surgical instruments, for example endoscopes, resectoscopes, cystoscopes or the like. An Albarran module can be used, for example, to position flexible forceps at an angle inside a patient in a specific and controlled manner. For this purpose, the Albarran module has, exactly like an endoscope for example, a rod-shaped or tubular shaft which is to be guided with a distal end into the body of the patient. At a proximal end of the Albarran module, outside the patient, the shaft is connected to a main body. By way of this main body, further instruments or tools, for example an optical system, wires or the like, can be guided into the patient through the shaft via various openings or ports.

At the distal end of the shaft, the Albarran module has a lever, the so-called Albarran lever. This lever is movable and can be actuated or pivoted via a toggle on the main body. For this purpose, the lever is coupled mechanically to the toggle along the shaft. This mechanical coupling can involve either a rod or a pull wire. Generally, the lever is connected to the toggle via two pull wires. It is conceivable that both pull wires serve equally to pivot the lever to and fro, or different movements of the lever via the toggle can be effected via both pull wires.

For reliable operation of the Albarran lever, the pull wires have to be braced inside the main body, in a drive body within the latter. That is to say, the pull wires are screwed with mechanical tensioning during assembly. For this purpose, the pull wires in known Albarran modules are each tensioned by a grub screw. To ensure that the grub screws are able to brace the respective pull wire, the wire has to be made deformable by means of annealing. This step is particularly awkward, since the wire already placed in the instrument has to be subjected to sufficiently high thermal energy in the main body and then braced with the grub screw. Since this bracing has to be done from the side, i.e. transversely with respect to a longitudinal axis of the shaft, this assembly step has to take place before the installation of the toggle or of a toggle axle. The grub screws are screwed in the drive body via the free openings for the toggles. All in all, this assembly proves very difficult and complicated and is therefore prone to error. If the main body of the Albarran module does not permit this lateral access to the pull wire, this type of bracing cannot be carried out.

The object of the invention is to make available an Albarran module, a drive body, and a method for bracing a pull wire, by which method the pull wire can be braced in a particularly simple and reliable manner.

Said object is achieved by the features of claim 1. Provision is accordingly made that the tensioning means for bracing the at least one pull wire is connectable to the drive body parallel to a longitudinal axis of a shaft. By this parallel bracing of the pull wire, lateral access to the pull wire is no longer necessary. Rather, the pull wire or the pull wires can be braced in a simple manner from the direction of the proximal end of the drive body. At its proximal end, the drive body generally has a cap, which can be easily detached from the drive body. By this bracing of the pull wire parallel to the longitudinal axis of the shaft, it is possible to achieve particularly simple and reliable bracing.

Preferably, according to the invention, provision can also be made that the tensioning means is a screw which can be screwed parallel to the shaft in the drive body or with a pull-wire carrier in the drive body, wherein the screw can be screwed into the drive body from a proximal side of the drive body, preferably from an opened proximal side of the drive body. By this screwing of the pull wire or of the pull wires along the shaft axis from the direction of the proximal end, a heating of the wire for bracing purposes becomes superfluous. This simplifies the overall assembly of the Albarran module.

In particular, according to the invention, provision can also be made that a screw head of the screw is coupled in terms of movement to a cover, wherein, by tightening of the screw, the cover is pulled into the drive body or into the pull-wire carrier and can be braced between the cover and the pull-wire carrier of the at least one pull wire. By way of the screw, therefore, a defined force can be applied for bracing the wire between the cover and the pull-wire carrier. This defined pretensioning ensures a high degree of reliability of the mechanical connection to the Albarran lever.

According to the invention, provision can also be made that the cover has a trapezoid cross section or is configured as a truncated pyramid, wherein the trapezoid cross section or the truncated pyramid converges in the distal direction of the shaft, and the drive body or the pull-wire carrier has a corresponding receptacle for receiving the cover. The cross section of the cover can in particular describe an isosceles or other trapezoid. This corresponding shaping of the cover and of the pull-wire carrier permits particularly efficient and secure bracing of the wire. By tightening of the screw, the cover is pulled automatically into the correspondingly shaped receptacle of the pull-wire carrier. In this bracing process, the wire or wires need to be held tensioned in order to achieve the desired mechanical tensioning between the toggle and the lever. As a result of the polygonal, preferably rectangular, cross section of the cover, as viewed in the shaft direction, it is possible to ensure that the cover does not co-rotate in the pull-wire carrier during the tightening of the screw; instead, the corners of the cover wedge in the receptacle of the pull-wire carrier. In order to better adapt to the shape of the drive body or of the pull-wire carrier and optimally utilize the available space, it is conceivable that at least one side of the cover is convex, wherein the convex shape can correspond to the shape of the drive body.

In a further illustrative embodiment of the invention, provision can be made that the circumferential surface of the cover is structured or roughened in order to increase the frictional resistance between the circumferential surface and the wire and the receptacle for bracing purposes. The roughening can also take place by abrasive blasting, for example. This roughening avoids a situation in which the pull wires are pulled out of the drive body as a result of increased force acting on the Albarran lever.

In a particularly advantageous illustrative embodiment of the invention, provision can be made that the at least one pull wire and the screw for bracing the wire in the drive body are arranged below an axle of the toggle oriented transversely with respect to the longitudinal axis of the shaft. By virtue of this geometry or positioning of the bracing means, the main body provides space for further ports or openings in the main body for the insertion of further tools.

Preferably, provision can also be made that, in order to brace the at least one pull wire, a distal end of the wire can be pulled through the drive body or through at least one opening in the pull-wire carrier, and, by screwing the cover, the wire end can be braced between the cover and the receptacle.

A drive body for achieving said object has the features of claim 8. Accordingly, provision is made that the drive body is designed according to at least one of claims 1 through 7.

A method for achieving said objects has the measures of claim 9. Accordingly, provision is made, according to the invention, that the pull wire is braced parallel to a longitudinal axis of the Albarran module by a tensioning means.

In addition, provision can be made, according to the invention, that one pull wire, in particular two pull wires, is/are guided through the drive body or a pull-wire carrier, and proximal ends of the pull wires are braced by tightening the tensioning means between a receptacle in the pull-wire carrier and a circumference of the tensioning means, in particular of a cover which is drawn tight by a screw.

A preferred illustrative embodiment of the present invention is explained in more detail below with reference to the drawing, in which.

Figure 1:
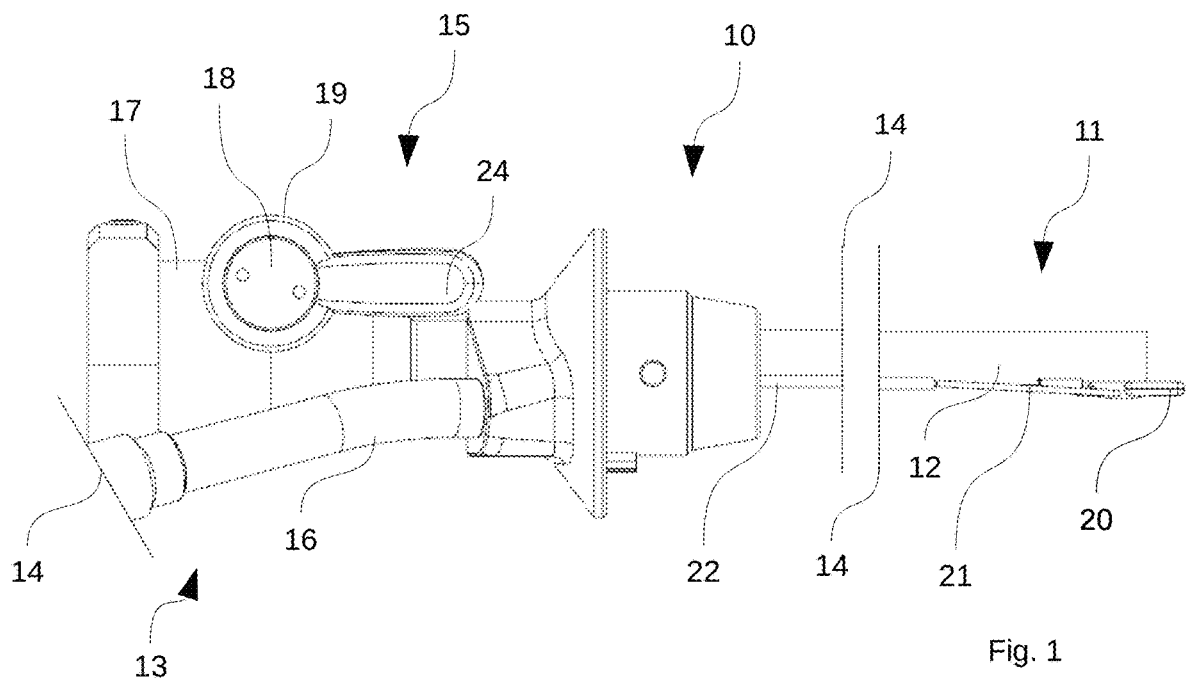
FIG. 1 shows a schematic view of an Albarran module.

FIG. 1 shows a possible illustrative embodiment of an Albarran module 10 according to the invention. For the sake of clarity, only a distal end 11 of a shaft 12 and a proximal end 13 of the Albarran module 10 are shown. The elongate, tubular shaft 12 is reproduced only in part by way of the section lines 14. This reduced depiction suffices for an understanding of the invention, since the portion of the shaft 12 not shown does not have any features essential to the invention.

The proximal end 13 of the Albarran module 10 is formed by a main body 15. This main body 15 is connected directly to the shaft 12. While the elongate shaft 12 is introduced into the interior of the patient's body during a treatment or an operation, the main body 15 remains outside the body and serves for the provision of various tools or aids for performing the operation. For this purpose, the main body 15 is assigned, for example, two tubular ports 16 through which, during the operation, tools (not shown) or other aids can be guided via the shaft 12 to the distal end 11 of the Albarran module 10, to the site of the operation. Once again for the sake of clarity, the proximal ends of the ports 16 and any subsequent valves are not shown. As has been described above for the shaft, these too are features that are not essential to the description of the invention.

Furthermore, the main body 15 has a drive body 17. Through this drive body 17, a toggle axle 18 of a toggle 19 runs perpendicular to a longitudinal axis of the Albarran module 10 or of the shaft 12. By the actuation of this lever-like toggle 19 or by rotation of the toggle 19 about the toggle axle 18, an Albarran lever 20 at the distal end 11 of the Albarran module 10 can be actuated. This Albarran lever 20 serves as an aid during the operation or the treatment. By actuation of this lever 20, further tools (not shown), which have been introduced into the body through other surgical instruments such as endoscopes or cystoscopes, can be operated with assistance. By adjusting the Albarran lever 20 in the clockwise direction, it is possible, for example, to move flexible forceps within the interior of the body.

Figure 2:
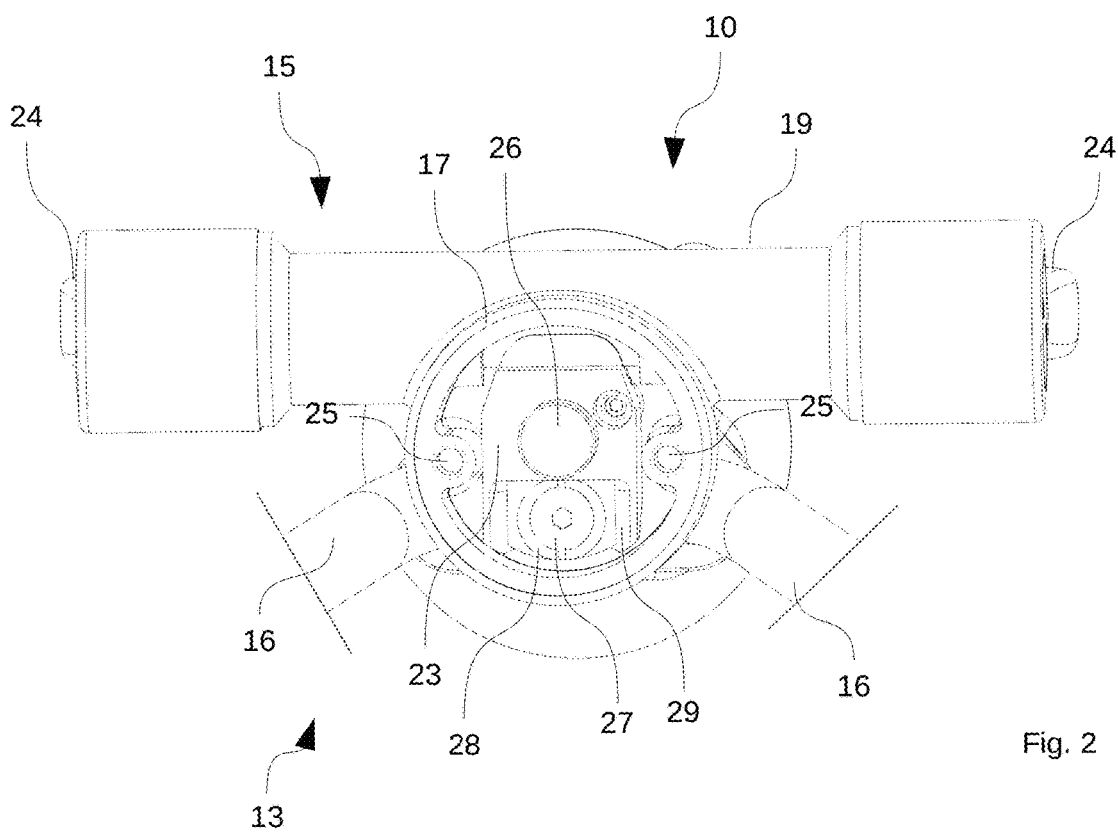
FIG. 2 shows a view of a proximal end of the Albarran module according to FIG. 1.

For the actuation of the Albarran lever 20, the drive body 17 or the toggle 19 is coupled in terms of movement to one or two pull-wires 21. Said pull-wire 21 can be guided either inside the shaft 12 or through a tube 22 outside the shaft 12. This tube 22 extends, parallel to the shaft 12, from the proximal end 13 to the distal end 11 or the Albarran lever 20. There, the pull wire 21 is coupled to the Albarran lever 20 in such a way that an actuation of the Albarran lever 20 is possible. At a proximal end of the pull wire 21, the latter is connected in the drive body 17 or to a pull-wire carrier 23. The pull-wire 21 is braced between the pull-wire carrier 23 and the Albarran lever 20, which is to say that the at least one pull-wire 21 is assembled with mechanical tensioning between the pull-wire carrier 23 and the Albarran lever 20 inside the main body 15 or the tube 22 or the shaft 12. By actuation of the toggle 19 about the toggle axle 18, the at least one pull-wire 21 is further tensioned, such that the Albarran lever 20 rotates about a pivot axis. As soon as the toggle 19 is rotated in an opposite direction, the mechanical tensioning of the pull-wire 21 subsides and the Albarran lever 20 moves back to its starting position. For the actuation of the toggle 19, the latter has two actuation means 24, as can be seen in FIG. 2. These lever-like actuation means 24 are assigned to the toggle 19 on both sides of the main body 15.

FIG. 2 allows a view of an open proximal end of the main body 15 or the drive body 17. A cap (not shown) can be fitted onto this open end of the main body 15 and can be closed by means of screws and the threaded bores 25. Arranged centrally in the drive body 17 is a channel 26 which extends through the whole Albarran module 10 and through the shaft 12 as far as the distal end 11. An optical system, for example, can be guided through this channel 26 for performing an operation. This optical system (not shown) serves, for example, to monitor the operation or to control the Albarran lever 20 in a specific way.

Figure 3:
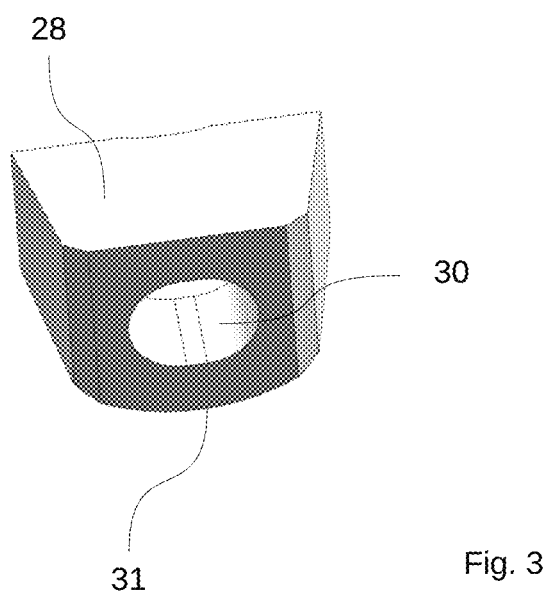
FIG. 3 shows a perspective view of a cover part.

Below the channel 26 and below the toggle axle 18, the pull-wire carrier 23 has a screw 27, in particular a countersunk-head screw. This screw 27 is screwed into the drive body 17, specifically parallel to the longitudinal axis of the shaft 12. With the screw 27, a cover 28 (FIG. 3) is inserted into or locked in a receptacle 29 of the pull-wire carrier 23. For this purpose, the screw 27 is guided through a bore 30 through the cover 28. This cover 28 can be of a conical shape, wherein its circumference converges toward the distal end 11. However, it is also conceivable that the cover 28 has a trapezoid cross section or is configured in the shape of a truncated pyramid. The trapezoid cross section or the truncated pyramid of the cover 28 likewise converges in the distal direction of the shaft (FIG. 3). For form-fit engagement, the drive body 17 and the pull-wire carrier 23 have a receptacle 29 corresponding to the shape of the cover 28. This corresponding shaping of the cover 28 and of the pull-wire carrier 23 permits particularly efficient and secure bracing of the wire, particularly by form-fit engagement. By tightening of the screw 27, the cover 28 is pulled automatically into the correspondingly shaped receptacle 29 of the pull-wire carrier 23. The polygonal, preferably rectangular cross section of the cover 28 ensures that the cover 28 does not co-rotate during the tightening of the screw 27. On account of the shape, the cover 28 wedges in the receptacle 29 of the pull-wire carrier 23. The illustrative embodiment of the cover 28 shown as an example in FIG. 3 has a convex side wall 31. By this shaping of the side wall 31, the cover 28 can better adapt to the shape of the drive body 17 or of the pull-wire carrier 23.

In the illustrative embodiment of the Albarran module 10 shown here, the pull wire 21 is assembled by being pulled through the tube 22 and the main body 15 or the drive body 17 from the distal end 11 of the Albarran module 10. The proximal ends of the pull wires 21 are then pulled through one opening or two openings in the pull-wire carrier 23, parallel to the threaded bore of the screw 27. While the two pull wires 21 are kept mechanically tensioned, the screw 27 is screwed along with the cover 28 into the receptacle 29. In this way, the pull wires 21 are braced between the recess 29 and the circumference of the cover 28. This bracing can be achieved particularly easily, since no further tools or method steps are needed. By the targeted application of a defined torque to the screw 27, the pull wires 21 can be braced with a high degree of precision and reliability. After the free ends of the pull wires 21 have been removed, the cap can be screwed onto the main body 15. In order to increase the tensioning force acting on the pull wires 21, the circumference of the cover 28 can be roughened. By means of this roughening, a frictional force between the receptacle 29, the cover 28 and the wires 21 can be generated, which leads to a greater bracing force.

It is expressly noted that the features described here are not limited to the use of the depicted illustrative embodiment of an Albarran module 10. Rather, it is conceivable that the features and measures according to the invention can also be used in connection with other surgical instruments.

LIST OF REFERENCE SIGNS

Albarran module 30 bore
11 distal end 31 side wall
12 shaft
13 proximal end
14 section line
main body
16 port
17 drive body
18 toggle axle
19 toggle
Albarran lever
21 pull wire
22 tube
23 pull-wire carrier
24 actuation means
threaded bore
26 channel
27 screw
28 cover
29 receptacle

The invention claimed is:

1. An Albarran module comprising:
   a shaft including a distal end and a proximal end;
   a main body with a drive body arranged at the proximal end of the shaft;
   an Albarran lever arranged at the distal end of the shaft;
   a toggle arranged on the drive body;
   a screw that is coupled to a cover and configured to connect to the drive body parallel to a longitudinal axis of the shaft;
   at least one pull wire including a proximal end that is braced in the drive body by the screw;
   a pull-wire carrier arranged within the drive body, wherein:
   a longitudinal axis of the screw is parallel to a longitudinal axis of the shaft in the drive body and a longitudinal axis of the pull-wire carrier in the drive body; and
   the screw is screwed into the drive body from a proximal side of the drive body; and
   when the screw is tightened, the cover is pulled into one of the drive body and the pull-wire carrier, and the at least one pull wire is configured to be braced between the cover and a receptacle of the pull-wire carrier, the cover being polygon-shaped.

2. The Albarran module as claimed in claim 1, wherein a screw head of the screw is coupled and configured to move together with the cover, and
   when the screw is tightened, the cover is pulled into the drive body or into the pull-wire carrier and the screw head is positioned such that it is braced between the cover and the pull-wire carrier.

3. The Albarran module as claimed in claim 2, wherein the cover has a trapezoid cross section or is configured as a truncated pyramid, wherein the trapezoid cross section or the truncated pyramid converges in a distal direction of the shaft, and the receptacle of the pull-wire carrier is configured to receive the cover.

4. The Albarran module as claimed in claim 2, wherein a circumferential surface of the cover is structured or roughened in order to increase a frictional resistance between the circumferential surface, the wire and the receptacle.

5. The Albarran module as claimed in claim 1, wherein the at least one pull wire and the screw for bracing the wire in the drive body are arranged below an axle of the toggle oriented transversely with respect to the longitudinal axis of the shaft.

6. The Albarran module as claimed in claim 2, wherein, in order to brace the at least one pull wire, a proximal end of the wire can be pulled through the drive body or through at least one opening in the pull-wire carrier, and, by screwing the cover.

7. The Albarran module as claimed in claim 1,
   wherein the screw is screwed into the drive body from an opened end of the drive body at the proximal side of the drive body.

* * * * *